United States Patent
Gomez et al.

(10) Patent No.: US 9,012,612 B2
(45) Date of Patent: Apr. 21, 2015

(54) INSECTICIDAL COMPOSITION AND PROCESSES RELATED THERETO

(75) Inventors: Luis E. Gomez, Carmel, IN (US); Eswin Castaneda, Mixco (GT); Leonardo Paniagua, Madrid (ES)

(73) Assignee: Dow AgroSciences LLC, Indianapolis, IN (US)

( * ) Notice: Subject to any disclaimer, the term of this patent is extended or adjusted under 35 U.S.C. 154(b) by 475 days.

(21) Appl. No.: 13/359,526

(22) Filed: Jan. 27, 2012

(65) Prior Publication Data

US 2012/0196820 A1    Aug. 2, 2012

Related U.S. Application Data

(60) Provisional application No. 61/437,137, filed on Jan. 28, 2011.

(51) Int. Cl.
| | | |
|---|---|---|
| *A01N 63/02* | (2006.01) | |
| *A01N 45/02* | (2006.01) | |
| *C07H 15/24* | (2006.01) | |
| *A01N 25/00* | (2006.01) | |

(52) U.S. Cl.
CPC .............. *A01N 25/006* (2013.01); *C07H 15/24* (2013.01); *A01N 45/02* (2013.01); *A01N 63/02* (2013.01)

(58) Field of Classification Search
None
See application file for complete search history.

(56) References Cited

U.S. PATENT DOCUMENTS

| 6,001,346 A | 12/1999 | Delwiche et al. |
| 2005/0158355 A1 | 7/2005 | Yamashita |
| 2010/0004176 A1 | 1/2010 | Sampson et al. |
| 2010/0216730 A1 | 8/2010 | Boucher et al. |
| 2010/0303940 A1 | 12/2010 | Enan |

FOREIGN PATENT DOCUMENTS

| CN | 101125774 | * 2/2008 | ............... C05G 1/00 |
| WO | PCT/US2012/022811 | 1/2012 | |

OTHER PUBLICATIONS

English language abstract of CN101125774 (Feb. 2008) from Chemical Abstracts.*
English language machine translation of CN101125774 (Feb. 2008) from www.epo.org.*

* cited by examiner

*Primary Examiner* — Eric Olson
(74) *Attorney, Agent, or Firm* — Carl D. Corvin

(57) ABSTRACT

Insecticidal compositions comprising:
(a) a biodegradable carrier;
(b) an ammonium compound;
(c) a protein source comprising one or more proteins;
(d) a sugar source comprising one or more monosaccharides;
(e) one or more insecticides; and
(f) water;
are disclosed as well as uses thereof.

9 Claims, No Drawings

INSECTICIDAL COMPOSITION AND PROCESSES RELATED THERETO

CROSS-REFERENCE TO RELATED APPLICATIONS

This Application claims priority from U.S. provisional application 61/437,137 filed on Jan. 28, 2011. The entire content of this provisional application is hereby incorporated by reference into this Application.

FIELD OF THE INVENTION

The invention disclosed in this document is related to the field of insecticidal compositions and their use.

BACKGROUND OF THE INVENTION

Diptera or true flies are found on all continents including Antarctica. Flies are the most important arthropod vectors of disease in humans and other animals. In addition to serving as vectors for diseases, flies can cause health problems themselves. Still others are nuisance pests or carry filth, such as latrine flies (Chrysomyia, family Calliphoridae), which breed in excrement and garbage. Fruit flies (family Tephritidae) are among the most destructive agricultural pests in the world, destroying citrus crops and other fruit and vegetable crops at an alarming rate and forcing food and agriculture agencies to spend millions of dollars on control and management measures.

One example of this problem is the Mediterranean fruit fly, *Ceratitis capitata*. Native to Africa, this voracious pest has spread to Europe, the Middle East, Central and South America, Western Australia and Hawaii. Outbreaks of this pest have also been found in the Continental United States, including the fruit producing regions of California and Florida triggering quarantine actions to control them. Although a poor flier, it is readily carried by winds and can be shipped virtually anywhere in the world in or on infected plants and produce. The Mediterranean fruit fly attacks more than 260 different fruits, flowers, nuts and vegetables. Their preferred hosts are succulent fruits, especially fruit that are thin skinned, nearly ripened and that have a break in their surface. A typical adult female fly may lay between 1-10 eggs at a time into a fruit; furthermore, a female can lay about 800 eggs over her lifetime. Under warm conditions such as those found in many fruit growing regions of Florida and California, the eggs hatch into larvae between 36 and 72 hours later. Depending on the ambient conditions and the food source, larvae mature between 10 to 26 days after hatching. The Mediterranean fruit fly larvae are voracious eaters and larvae hatched into a piece of ripening fruit develop by consuming the fruit and, in the process, reduce the fruit to an inedible mass.

Therefore, for many reasons, including the above reasons, a need exists for new ways to control Diptera.

DETAILED DESCRIPTION OF THE INVENTION

This document discloses insecticidal compostions useful for controling Diptera or true flies, especially Mediterranean fruit fly.

These insecticidal compositions comprise:
(a) a biodegradable carrier;
(b) an ammonium compound;
(c) a protein source comprising one or more proteins;
(d) a sugar source comprising one or more monosaccharides;
(e) one or more insecticides; and
(f) water.

The biodegradable carrier are waxes, such as beeswax, lanolin, shellac wax, carnauba wax, lanolin, fruit wax (such as bayberry or sugar cane wax) candelilla wax, other waxes such as microcrystalline, ozocerite, ceresin, montan, vegetable based waxes such as soy wax, or hydrocarbon based waxes such as paraffin. Paraffin, which is easy to handle, has a practical melting point and is relatively inexpensive, is a preferred carrier. It is preferred if the carrier is in the form of an aqueous sprayable emulsion, preferably which adheres to plant bark or foliage, then slowly erodes from plant surfaces and biodegrades in the soil. The carrier is preferably made as described in U.S. Pat. No. 6,001,346, which is hereby incorporated by reference. Such carriers are available from ISCA TECHNOLOGIES, Inc. 1230 W. Spring St., Riverside, Calif. 92507, United States of America under the trademark of SPLAT™ (Specialized Pheromone & Lure Application Technology). This technology covers a biologically inert matrix for the release of semiochemicals and/or pesticides.

The ammonium compound is a compound that is attractive to flies because it can emit ammonia into the environment. Ammonium acetate, ammonium carbonate, ammonium bicarbonate, and ammonium sulfate can be used Ammonium acetate is more preferred than other ammonium compounds.

The protein source comprising one or more proteins is preferably a vegetable protein source, that is, a source comprising one or more proteins obtained from vegetables. While proteins from animals may be used, it is preferable to use those proteins that are obtained from vegetables. One such source is corn steep liquor ("CSL"). CSL is a liquid mixture comprising the water soluble components of corn steeped in water. It contains crude protein, amino acids, vitamins, sugars, organic acids, minerals, and other nutrients. It is available from a wide variety of producers.

The sugar source comprising one or more monosaccharides can be obtained from a wide variety of producers. While any monosaccharides that is digestible by flies may be used such as glucose, it is preferred if invert sugar is used. Invert sugar is a mixture of glucose and fructose. It can be obtained by splitting sucrose into its sugar components. Compared with its precursor, sucrose, inverted sugar is sweeter and compositions that invert sugar is mixed with tend to remain moister and are less prone to crystallization.

The one or more insecticides can be any insecticide, such as one from the following list—1,2-dichloropropane, abamectin, acephate, acetamiprid, acethion, acetoprole, acrinathrin, acrylonitrile, alanycarb, aldicarb, aldoxycarb, aldrin, allethrin, allosamidin, allyxycarb, alpha-cypermethrin, alpha-ecdysone, alpha-endosulfan, amidithion, aminocarb, amiton, amiton oxalate, amitraz, anabasine, athidathion, azadirachtin, azamethiphos, azinphos-ethyl, azinphos-methyl, azothoate, *Bacillus thuringiensis, Bacillus sphaericus,* barium hexafluorosilicate, barthrin, bendiocarb, benfuracarb, bensultap, beta-cyfluthrin, beta-cypermethrin, bifenthrin, bioallethrin, bioethanomethrin, biopermethrin, bistrifluron, borax, boric acid, bromfenvinfos, bromocyclen, bromo-DDT, bromophos, bromophos-ethyl, bufencarb, buprofezin, butacarb, butathiofos, butocarboxim, butonate, butoxycarboxim, cadusafos, calcium arsenate, calcium polysulfide, camphechlor, carbanolate, carbaryl, carbofuran, carbon disulfide, carbon tetrachloride, carbophenothion, carbosulfan, cartap, cartap hydrochloride, chlorantraniliprole, chlorbicyclen, chlordane, chlordecone, chlordimeform, chlordimeform hydrochloride, chlorethoxyfos, chlorfenapyr, chlorfenvinphos, chlorfluazuron, chlormephos, chloroform, chloropicrin, chlorphoxim, chlorprazophos, chlorpyrifos, chlorpyrifos-methyl, chlorthiophos, chromafenozide, cinerin I, cinerin II, cinerins, cismethrin, cloethocarb, closantel, clothianidin, copper acetoarsenite, copper arsenate, copper naphthenate, copper oleate, coumaphos, coumithoate, crotamiton, crotoxyphos, crufomate, cryolite, cyanofenphos, cyanophos, cyanthoate, cyantraniliprole, cyclethrin, cycloprothrin, cyfluthrin, cyhalothrin, cypermethrin, cyphenothrin, cyromazine, cythioate, DDT, decarbofuran, deltamethrin, demephion, demephion-O, demephion-S, demeton, demeton-methyl, demeton-O, demeton-O-methyl, demeton-S, demeton-S-methyl, demeton-S-methylsulphon, diafenthiuron, dialifos, diatomaceous earth, diazinon, dicapthon, dichlofenthion, dichlorvos, dicresyl, dicrotophos, dicyclanil, dieldrin, diflubenzuron, dilor, dimefluthrin, dimefox, dimetan, dimethoate, dimethrin, dimethylvinphos, dimetilan, dinex, dinex-diclexine, dinoprop, dinosam, dinotefuran, diofenolan, dioxabenzofos, dioxacarb, dioxathion, disulfoton, dithicrofos, d-limonene, DNOC, DNOC-ammonium, DNOC-potassium, DNOC-sodium, doramectin, ecdysterone, emamectin, emamectin benzoate, EMPC, empenthrin, endosulfan, endothion, endrin, EPN, epofenonane, eprinomectin, esdepalléthrine, esfenvalerate, etaphos, ethiofencarb, ethion, ethiprole, ethoate-methyl, ethoprophos, ethyl formate, ethyl-DDD, ethylene dibromide, ethylene dichloride, ethylene oxide, etofenprox, etrimfos, EXD, famphur, fenamiphos, fenazaflor, fenchlorphos, fenethacarb, fenfluthrin, fenitrothion, fenobucarb, fenoxacrim, fenoxycarb, fenpirithrin, fenpropathrin, fensulfothion, fenthion, fenthion-ethyl, fenvalerate, fipronil, flonicamid, flubendiamide (additionally resolved isomers thereof), flucofuron, flucycloxuron, flucythrinate, flufenerim, flufenoxuron, flufenprox, fluvalinate, fonofos, formetanate, formetanate hydrochloride, formothion, formparanate, formparanate hydrochloride, fosmethilan, fospirate, fosthietan, fufenozide, furathiocarb, furethrin, gamma-cyhalothrin, gamma-HCH, halfenprox, halofenozide, HCH, HEOD, heptachlor, heptenophos, heterophos, hexaflumuron, HHDN, hydramethylnon, hydrogen cyanide, hydroprene, hyquincarb, imidacloprid, imiprothrin, indoxacarb, iodomethane, IPSP, isazofos, isobenzan, isocarbophos, isodrin, isofenphos, isofenphos-methyl, isoprocarb, isoprothiolane, isothioate, isoxathion, ivermectin, jasmolin I, jasmolin II, jodfenphos, juvenile hormone I, juvenile hormone II, juvenile hormone III, kelevan, kinoprene, lambda-cyhalothrin, lead arsenate, lepimectin, leptophos, lindane, lirimfos, lufenuron, lythidathion, malathion, malonoben, mazidox, mecarbam, mecarphon, menazon, meperfluthrin, mephosfolan, mercurous chloride, mesulfenfos, metaflumizone, methacrifos, methamidophos, methidathion, methiocarb, methocrotophos, methomyl, methoprene, methothrin, methoxychlor, methoxyfenozide, methyl bromide, methyl isothiocyanate, methylchloroform, methylene chloride, metofluthrin, metolcarb, metoxadiazone, mevinphos, mexacarbate, milbemectin, milbemycin oxime, mipafox, mirex, molosultap, monocrotophos, monomehypo, monosultap, morphothion, moxidectin, naftalofos, naled, naphthalene, nicotine, nifluridide, nitenpyram, nithiazine, nitrilacarb, novaluron, noviflumuron, omethoate, oxamyl, oxydemeton-methyl, oxydeprofos, oxydisulfoton, para-dichlorobenzene, parathion, parathion-methyl, penfluron, pentachlorophenol, permethrin, phenkapton, phenothrin, phenthoate, phorate, phosalone, phosfolan, phosmet, phosnichlor, phosphamidon, phosphine, phoxim, phoxim-methyl, pirimetaphos, pirimicarb, pirimiphos-ethyl, pirimiphos-methyl, potassium arsenite, potassium thiocyanate, pp'-DDT, prallethrin, precocene I, precocene II, precocene III, primidophos, profenofos, profluralin, profluthrin, promacyl, promecarb, propaphos, propetamphos, propoxur, prothidathion, prothiofos, prothoate, protrifenbute, pymetrozine, pyraclofos, pyrafluprole, pyrazophos, pyresmethrin, pyrethrin I, pyrethrin II, pyrethrins, pyridaben, pyridalyl, pyridaphenthion, pyrifluquinazon, pyrimidifen, pyrimitate, pyriprole, pyriproxyfen, quassia, quinalphos, quinalphos-methyl, quinothion, rafoxanide, resmethrin, rotenone, ryania, sabadilla, schradan, selamectin, silafluofen, silica gel, sodium arsenite, sodium fluoride, sodium hexafluorosilicate, sodium thiocyanate, sophamide, spinetoram, spinosad, spiromesifen, spirotetramat, sulcofuron, sulcofuron-sodium, sulfluramid, sulfotep, sulfoxaflor, sulfuryl fluoride, sulprofos, tau-fluvalinate, tazimcarb, TDE, tebufenozide, tebufenpyrad, tebupirimfos, teflubenzuron, tefluthrin, temephos, TEPP, terallethrin, terbufos, tetrachloroethane, tetrachlorvinphos, tetramethrin, tetramethylfluthrin, theta-cypermethrin, thiacloprid, thiamethoxam, thicrofos, thiocarboxime, thiocyclam, thiocyclam oxalate, thiodicarb, thiofanox, thiometon, thiosultap, thiosultap-disodium, thiosultap-monosodium, thuringiensin, tolfenpyrad, tralomethrin, transfluthrin, transpermethrin, triarathene, triazamate, triazophos, trichlorfon, trichlormetaphos-3, trichloronat, trifenofos, triflumuron, trimethacarb, triprene, vamidothion, vaniliprole, XMC, xylylcarb, zeta-cypermethrin, and zolaprofos.

Preferable, the insecticide used is an insecticide that can be used in organic farming. Organic farming methods are internationally regulated and enforced by many nations, based in large part on the standards set by the international organizations. Since 1990, the market for organic products has grown, reaching $51 billion in 2008. Naturally-derived insecticides allowed for use on organic farms include *Bacillus thuringiensis*, pyrethrum, spinosad, neem, and rotenone.

The components of this insecticidal composition can be mixed in any manner known in the art. The amount of each component to mix is shown in Table 1.

TABLE ONE

Weight Percents (based on the weight of these components)

|  | Broad | Broader | Broadest |
|---|---|---|---|
| Insecticide | 0.9-1.3 | 0.6-1.5 | 0.2-1.6 |
| Sugar Source | 18-29 | 14-36 | 10-44 |
| Protein Source | 8-12 | 6-16 | 4-20 |
| Ammonium Compound | 0.9-1.4 | 0.7-1.8 | 0.5-2 |
| Water | 6-11 | 5-15 | 4-18 |
| Biodegradable Carrier | 30-50 | 25-60 | 25-75 |

A variety of other items may be incorporated into the insecticidal composition. These items typically change and/or enhance the physical characteristics of the composition. These items are, among others, plasticizers, volatility suppressants, antioxidants, lipids, various ultraviolet blockers and absorbers, or antimicrobials, typically added in amounts from about 0.001% to about 10%, more typically between 1-6%, by weight.

Plasticizers, such as glycerin or soy oil, affect physical properties of the composition and may be included in a formulation in order to extend its resistance to degradation in the field. Antioxidants, such as vitamin E, BHA (butylated hydroxyanisole), BHT (butylated hydroxytoluene), and other antioxidants may be added in amounts from about 0.1% to about 3%, by weight. An ultraviolet blocker, such as beta-carotene or p-aminobenzoic acid may be present in the composition in amounts ranging from about 1% to about 3%, by weight. Antimicrobial reagent, such as potassium sorbate, nitrates, nitrites, and propylene oxide, may be added in amounts from 0.1% to about 2% by weight. Other items such as adjuvants, humectants, viscosity modifiers can also be added. (These weight percents are based on the total weight of the insecticidal composition)

This invention is useful for crop protection by providing a method for control and management of flies. Such control is achieved by delivering the composition to potentially infested areas to be protected or to infested areas where flies need to be controlled, such as by eradication or the reduction of their numbers to acceptable levels. The amount of insecticidal composition to apply to such area is generally from about 1.0 to 4.0 kilograms per acre. A major feature of this invention is sprayability and biodegradability of the composition. The composition can be sprayed or squirted from ground level and thus applied higher in the tree than a worker could reach by himself without help.

The insecticidal compositions can be used against a wide variety of the members of Order Diptera especially the families Tephritidae, Drosophilidae, Lonchaeidae, and/or Muscidae. A non-exhaustive list of particular genera includes, but is not limited to, *Aedes* spp., *Agromyza* spp., *Anastrepha* spp., *Anopheles* spp., *Bactrocera* spp., *Ceratitis* spp., *Chrysops* spp., *Cochliomyia* spp., *Contarinia* spp., *Culex* spp., *Dasineura* spp., *Delia* spp., *Drosophila* spp., *Fannia* spp., *Hylemyia* spp., *Liriomyza* spp., *Musca* spp., *Phorbia* spp., *Rhagoletis* spp., *Tabanus* spp., and *Tipula* spp. A non-exhaustive list of particular species includes, but is not limited to, *Agromyza frontella, Anastrepha suspensa, Anastrepha ludens, Anastrepha obliqa, Bactrocera cucurbitae, Bactrocera dorsalis, Bactrocera invadens, Bactrocera zonata, Ceratitis capitata, Dasineura brassicae, Delia platura, Drosophila suzukii, Fannia canicularis, Fannia scalaris, Gasterophilus intestinalis, Gracillia perseae, Haematobia irritans, Hypoderma lineatum, Liriomyza brassicae, Melophagus ovinus, Musca autumnalis, Musca domestica, Oestrus ovis, Oscinella frit, Pegomya betae, Psila rosae, Rhagoletis cerasi, Rhagoletis pomonella, Rhagoletis mendax, Sitodiplosis mosellana*, and *Stomoxys calcitrans*.

EXAMPLES

The examples are for illustration purposes and are not to be construed as limiting the invention disclosed in this document to only the embodiments disclosed in these examples.

Example 1

Five compositions (A-E) were made by mixing the components in the proportions indicated in Table 2 at room temperature using a spatula. The biodegradable carrier was made in accordance with U.S. Pat. No. 6,001,346.

TABLE 2

| Weight percents of Components | | | | |
|---|---|---|---|---|
| Component | A | B | C | D |
| Spinosad | 0.42 | 0.815 | 1.21 | 1.605 |
| Invert Sugar | 41.2 | 30.9 | 20.6 | 10.3 |
| Corn Steep Liquor | 17.6 | 13.2 | 8.8 | 4.4 |
| Ammonium Acetate | 2 | 1.5 | 1 | 0.5 |
| Polysorbate 60 | 2 | 1.5 | 1 | 0.5 |
| Propylene Glycol | 2 | 1.5 | 1 | 0.5 |
| Xanthan Gum | 0.6 | 0.45 | 0.3 | 0.15 |
| Soybean Oil | 0.4 | 0.3 | 0.2 | 0.1 |
| Water | 14.18 | 10.635 | 7.09 | 3.545 |
| Biodegradable Carrier (Paraffin) | 19.6 | 39.2 | 58.8 | 78.4 |

Example 2

Fifteen 5μl droplets of the compositions were applied to coffee leaves on live coffee plants using a micro-pipette. A sufficient number of leaves (minimum of 240) were treated with each of the compositions to assure availability of aged product to cover 5 repetitions per treatment for 4 weeks after application. Treated leaves were tagged on the day that the compositions were applied in order to be able to identify them when needed after the compositions were aged. Coffee plants treated with various test compositions were left outside under normal environmental conditions (light, temperature, rain, etc). The compositions were allowed to aged under normal conditions and leaves were recovered from aging plants to test the performance of the different compositions (A-D).

Mediterranean fruit flies were used as test insects. After their emergence, all flies were fed regular laboratory food and the flies were aged for 5 to 7 days before they were used in the bioassay. Once in the bioassays, all flies were offered a 2% sugar solution as a food source. 1-ft$^3$ cages (30 by 30 by 30 cm high/length/width) were used for the assays. Four leaves were inserted into each cage prior to introducing flies into the cage. Fifty total cages were used and 60 total flies were included in each cage (30 males and 30 females).

Five repetitions of each treatment were carried out (1 cage =1 repetition). The results are indicated in Table 3.

TABLE 3

| Percent Control of Adult Mediterranean fruit flies 8 hrs after exposure | | | | |
|---|---|---|---|---|
| Composition | Week 1 | Week 2 | Week 3 | Week 4 |
| A | 97.28a* | 96.25a | 52.19b | 64.79b |
| B | 94.33ab | 91.44a | 63.68b | 56.16bc |
| C | 84.64d | 86.68a | 92.03a | 79.86a |
| D | 75.12d | 46.94b | 31.3c | 9.26d |

*Duncan, α = 0.05
*Numbers followed by different letters are significantly different according to Duncan's Multiple range test at the 0.05 level As can be seen in Table 3, the most dramatic differences between the various compositions are apparent at weeks 3 and 4. By this time, the composition designated as C in Table 1 demonstrates greater control over the flies exposed to the treated leaves than other compositions such as D. The letters behind the numbers indicated that these numbers were statistically significantly different from the other numbers with different letters. So even though there was 33 percent more insecticide in composition D than composition C, composition D was more than 800 percent better at controlling Mediterranean fruit flies than composition E at the 4 week test.

We claim:

1. An insecticidal composition consisting essentially of:
   (a) about 45-60 weight percent of a biodegradable carrier;
   (b) about 0.9-1.4 weight percent of an ammonium compound;
   (c) about 8-12 weight percent of corn steep liquor;
   (d) about 18-29 weight percent of invert sugar;
   (e) 0.9-1.3 weight percent of Spinosad; and
   (f) about 6-11 weight percent of water
   where said weight percents are based on the weight of components (a)-(f).

2. A process to apply a composition according to claim 1 said process comprising applying said composition according to claim 1, to an area to control Diptera in an amount sufficient to control such pest.

3. A process according to claim 2 wherein said Diptera is from the family Tephritidae.

4. A process according to claim 2 wherein said Diptera is from the family Drosophilidae.

5. A process according to claim 2 wherein said Diptera is from the family Lonchaeidae.

6. A process according to claim 2 wherein said Diptera is from the family Muscidae.

7. A process according to claim 2 wherein said Diptera is selected from *Aedes* spp., *Agromyza* spp., *Anastrepha* spp., *Anopheles* spp., *Bactrocera* spp., *Ceratitis* spp., *Chrysops* spp., *Cochliomyia* spp., *Contarinia* spp., *Culex* spp., *Dasineura* spp., *Delia* spp., *Drosophila* spp., *Fannia* spp., *Hylemyia* spp., *Liriomyza* spp., *Musca* spp., *Phorbia* spp., *Rhagoletis* spp., *Tabanus* spp., and *Tipula* spp.

8. A process according to claim 2 wherein said Diptera is selected from *Agromyza frontella, Anastrepha suspensa, Anastrepha ludens, Anastrepha obliqa, Bactrocera cucurbitae, Bactrocera dorsalis, Bactrocera invadens, Bactrocera zonata, Ceratitis capitata, Dasineura brassicae, Delia platura, Drosophila suzukii, Fannia canicularis, Fannia scalaris, Gasterophilus intestinalis, Gracillia perseae, Haematobia irritans, Hypoderma lineatum, Liriomyza brassicae, Melophagus ovinus, Musca autumnalis, Musca domestica, Oestrus ovis, Oscinella frit, Pegomya betae, Psila rosae, Rhagoletis cerasi, Rhagoletis pomonella, Rhagoletis mendax, Sitodiplosis mosellana*, and *Stomoxys calcitrans*.

9. A process according to claim 2 wherein said Diptera is Ceratitis capitata.

\* \* \* \* \*